(12) United States Patent
Higuchi et al.

(10) Patent No.: US 7,485,465 B2
(45) Date of Patent: Feb. 3, 2009

(54) MICRO PLATE TREATING DEVICE AND MICRO PLATE CARRYING METHOD

(75) Inventors: Akira Higuchi, Fukuoka (JP); Eiji Watanabe, Fukuoka (JP)

(73) Assignee: Panasonic Corporation, Osaka (JP)

( * ) Notice: Subject to any disclaimer, the term of this patent is extended or adjusted under 35 U.S.C. 154(b) by 372 days.

(21) Appl. No.: 10/549,149

(22) PCT Filed: Apr. 5, 2005

(86) PCT No.: PCT/JP2005/006987

§ 371 (c)(1),
(2), (4) Date: Sep. 13, 2005

(87) PCT Pub. No.: WO2005/098454

PCT Pub. Date: Oct. 20, 2005

(65) Prior Publication Data

US 2006/0210446 A1    Sep. 21, 2006

(30) Foreign Application Priority Data

Apr. 7, 2004    (JP)    ............... 2004-112976

(51) Int. Cl.
G01N 35/02    (2006.01)
G01N 35/04    (2006.01)

(52) U.S. Cl. ............... 436/48; 436/43; 436/47; 436/49; 422/63; 422/65; 422/100; 141/129; 141/130; 53/109; 53/281

(58) Field of Classification Search .......... None
See application file for complete search history.

(56) References Cited

U.S. PATENT DOCUMENTS

| 3,844,896 | A | * | 10/1974 | Sharpe | 435/286.4 |
| 5,985,214 | A | * | 11/1999 | Stylli et al. | 422/65 |
| 6,360,792 | B1 | * | 3/2002 | Ganz et al. | 141/129 |
| 6,979,425 | B1 | * | 12/2005 | Ganz et al. | 422/100 |
| 2002/0119077 | A1 | * | 8/2002 | Shumate et al. | 422/100 |
| 2002/0176803 | A1 | * | 11/2002 | Hamel et al. | 422/100 |
| 2003/0044991 | A1 | * | 3/2003 | Haslam et al. | 436/47 |

FOREIGN PATENT DOCUMENTS

| JP | 11-223636 | 8/1999 |
| JP | 2002-340912 | 11/2002 |
| JP | 2004-85521 | 3/2004 |

* cited by examiner

Primary Examiner—Jill Warden
Assistant Examiner—P. Kathryn Wright
(74) Attorney, Agent, or Firm—McDermott Will & Emery LLP

(57) ABSTRACT

In a microplate processing apparatus that removes lid (11) of microplate (10) conveyed by microplate conveying mechanism (3) to perform a dispensing process by dispensing head (8), and that attaches lid (11) after the dispensing process is completed, lid (11) removed by lid removing mechanism (6) at first position (P1) is conveyed to third position (P3) located downstream, by microplate conveying mechanism (3), to be held by lid attaching mechanism (9), and then lid (11) is attached to microplate (10) having been conveyed to third position (P3), after the dispensing process is completed, while microplate (10) with this lid (11) having been attached is being lifted to processing position (P4) above microplate conveying mechanism (3), by microplate stage (12).

6 Claims, 8 Drawing Sheets

MICRO PLATE TREATING DEVICE AND MICRO PLATE CARRYING METHOD

This application is the U.S. National Phase under 35 U.S.C. § 371 of International Application No. PCT/JP2005/006987, filed Apr. 05, 2005, which in turn claims the benefit of Japanese Application No. 2004-112976, filed Apr. 07, 2004, the disclosures of which Applications are incorporated by reference herein in their entirety.

TECHNICAL FIELD

The present invention relates to a microplate processing apparatus capable of performing given processes for microplates, and to a method of conveying microplates in the microplate processing apparatus.

BACKGROUND ART

In fields such as drug screening and biotechnology, biochemical reactions of substances and the like are tested. In the testing, a microplate is used as a container for containing drug solution and test substances with which cultivation and biochemical reactions are performed. The testing, usually performed systematically targeted for a large number of samples, processes a plurality of microplates in one testing for dispensing operation, componential analysis, and others.

Under the circumstances, as disclosed in Japanese Patent Unexamined Publication No. H11-223636, such a structure is known that is equipped with a feeding device for stocking a plurality of microplates; and a plate conveying mechanism for conveying microplates extracted from the feeding device, as a dedicated processing apparatus for performing the above-mentioned processes automatically. In this conventional example, microplates are individually contained in a storage rack provided with a plurality of plate placing positions; when feeding, microplates are extracted one by one by means of a plate conveying mechanism of the ceiling-travel robot type, and are transferred to the dispensing stage; and microplates having undergone the dispensing operation are returned into the storage rack.

A well for containing liquid, provided in a microplate, is open at its top surface. Therefore, when storing a microplate with liquid injected into its well, having undergone the dispensing operation, a lidded microplate may be used for isolating the injected liquid from the outside atmosphere, depending on a purpose of testing. In such a case, the lid needs to be attached and detached when performing processes such as a dispensing operation for the microplate, and thus the microplate processing apparatus requires a function for attaching and detaching a microplate lid.

In the above-mentioned conventional example, for instance, the apparatus is equipped with a lid removing unit therein, and microplates individually move to the lid removing unit by the plate conveying mechanism every time before and after a dispensing operation is performed.

However, in the above-mentioned conventional example, only one set of lid removing unit is arranged at a fixed position. Consequently, a large number of microplates requiring being processed continuously make it difficult to attach and detach lids efficiently, which causes the entire processing to be inefficient.

SUMMARY OF THE INVENTION

A microplate processing apparatus according to the present invention has the following makeup.

A microplate processing apparatus that removes a microplate lid to perform a given process for the microplate, and attaches the lid after the process is completed, the apparatus equipped with a microplate conveying mechanism with a conveyor belt, for conveying the microplate in an order corresponding to a lid removing position, an intermediate position, and a lid attaching position, from upstream on a conveying path; a microplate positioning mechanism for extracting the microplate from the microplate conveying mechanism to position the microplate at a processing position where the above-mentioned process is performed, and for replacing the microplate from the relevant processing position to the microplate conveying mechanism, at the intermediate position; a processing unit for performing a given process for the microplate positioned at the processing position; a lid removing mechanism for removing the microplate lid at the lid removing position, and for placing the removed lid onto the conveying path of the microplate conveying mechanism; a lid attaching mechanism that picks up the lid conveyed from the lid removing position to the lid attaching position by the microplate conveying mechanism, from the microplate conveying mechanism, and attaches the picked up lid to the microplate conveyed to the lid attaching position; and a control unit for controlling the microplate conveying mechanism so that the lid placed on the conveying path by the lid removing mechanism is conveyed from the lid removing position to the lid attaching position, while the microplate is being extracted from the microplate conveying mechanism by the microplate positioning mechanism.

A method of conveying a microplate according to the present invention has the following steps.

A method of conveying a microplate in a microplate processing apparatus equipped with a microplate conveying mechanism with a conveyor belt, for conveying the microplate in an order corresponding to a lid removing position, an intermediate position, and a lid attaching position, from upstream on a conveying path, the method including a lid removing position conveying step for conveying the microplate with its lid attached, to the lid removing position, by the microplate conveying mechanism; a lid removing step for removing a microplate lid at the lid removing position; an intermediate position conveying step for conveying the microplate with its lid removed, to the intermediate position, by the microplate conveying mechanism; a positioning step for extracting the microplate conveyed to the intermediate position, from the microplate conveying mechanism, to position the microplate at a processing position; a lid placing step for placing the lid removed in the lid removing step, on the conveying path of the microplate conveying mechanism; a lid conveying step for conveying the lid placed on the conveying path, from the lid removing position to the lid attaching position, by the microplate conveying mechanism; a lid picking up step for picking up the lid conveyed to the lid attaching position, from the microplate conveying mechanism, and for holding the lid; a replacing step for replacing the microplate having undergone a given process at the processing position, to the microplate conveying mechanism, at the intermediate position; a lid attaching position conveying step for conveying the microplate replaced to the microplate conveying mechanism, from the intermediate position to the lid attaching position; a lid attaching step for attaching the lid held in the lid picking up step, to the microplate conveyed to the lid attaching position; and a carrying out step for carrying out the microplate with its lid attached, from the lid attaching position, by the microplate conveying mechanism.

According to the present invention, when performing a given process targeted for the microplate with its lid extracted at the lid removing position, adopting the following makeup allows attaching and detaching the lid to and from the microplate to be performed efficiently. That is, the microplate is to be extracted from the microplate conveying mechanism by the microplate positioning mechanism, and the removed lid is to be conveyed from the lid removing position to the lid attaching position while the microplate is being extracted from the microplate conveying mechanism.

DETAILED DESCRIPTION OF PREFERRED EMBODIMENT

Hereinafter, a description will be made for an embodiment of the present invention, using drawings.

Figure 1:
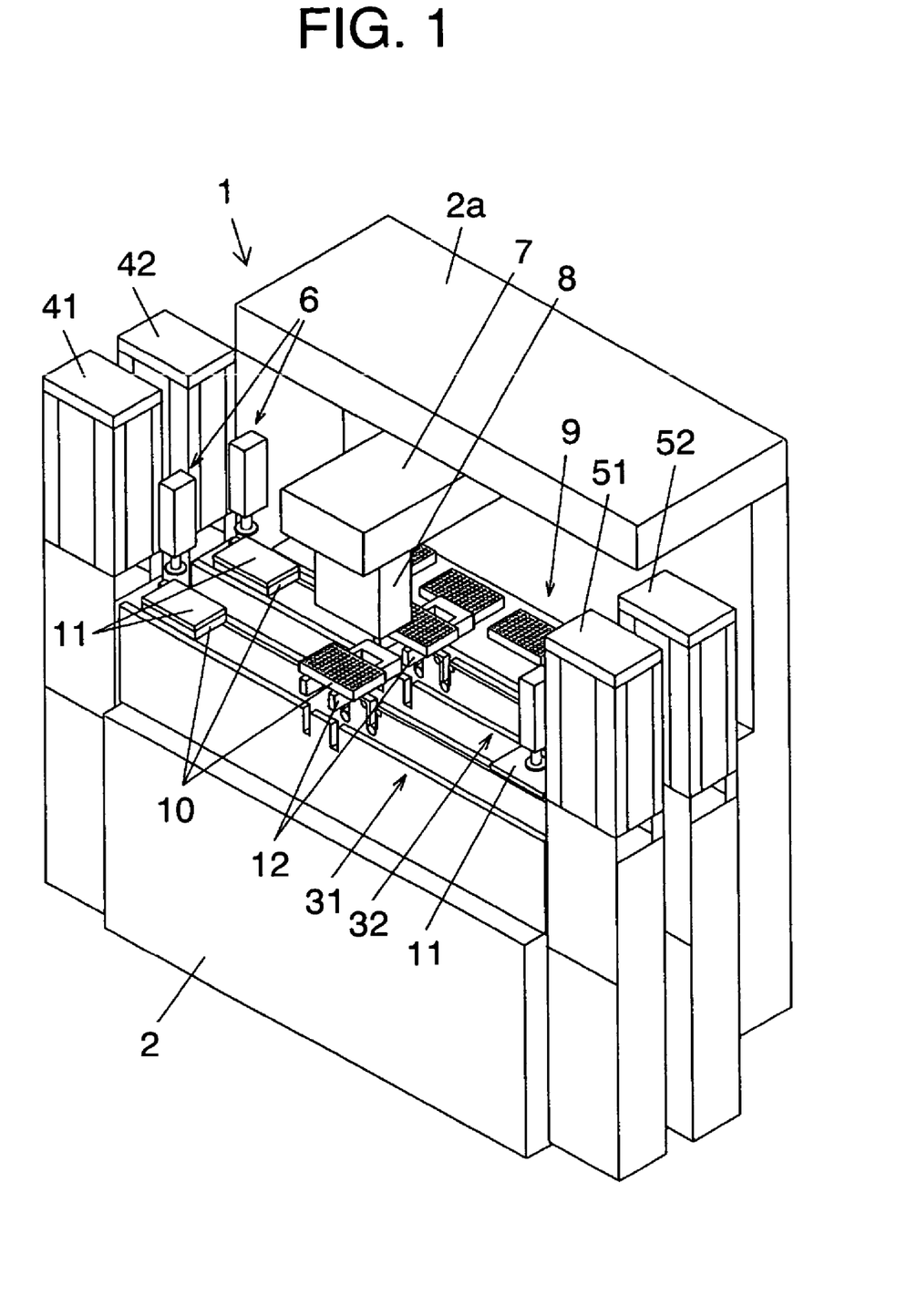
FIG. 1 is a perspective view of a microplate processing apparatus according to an embodiment of the present invention.
Figure 2:
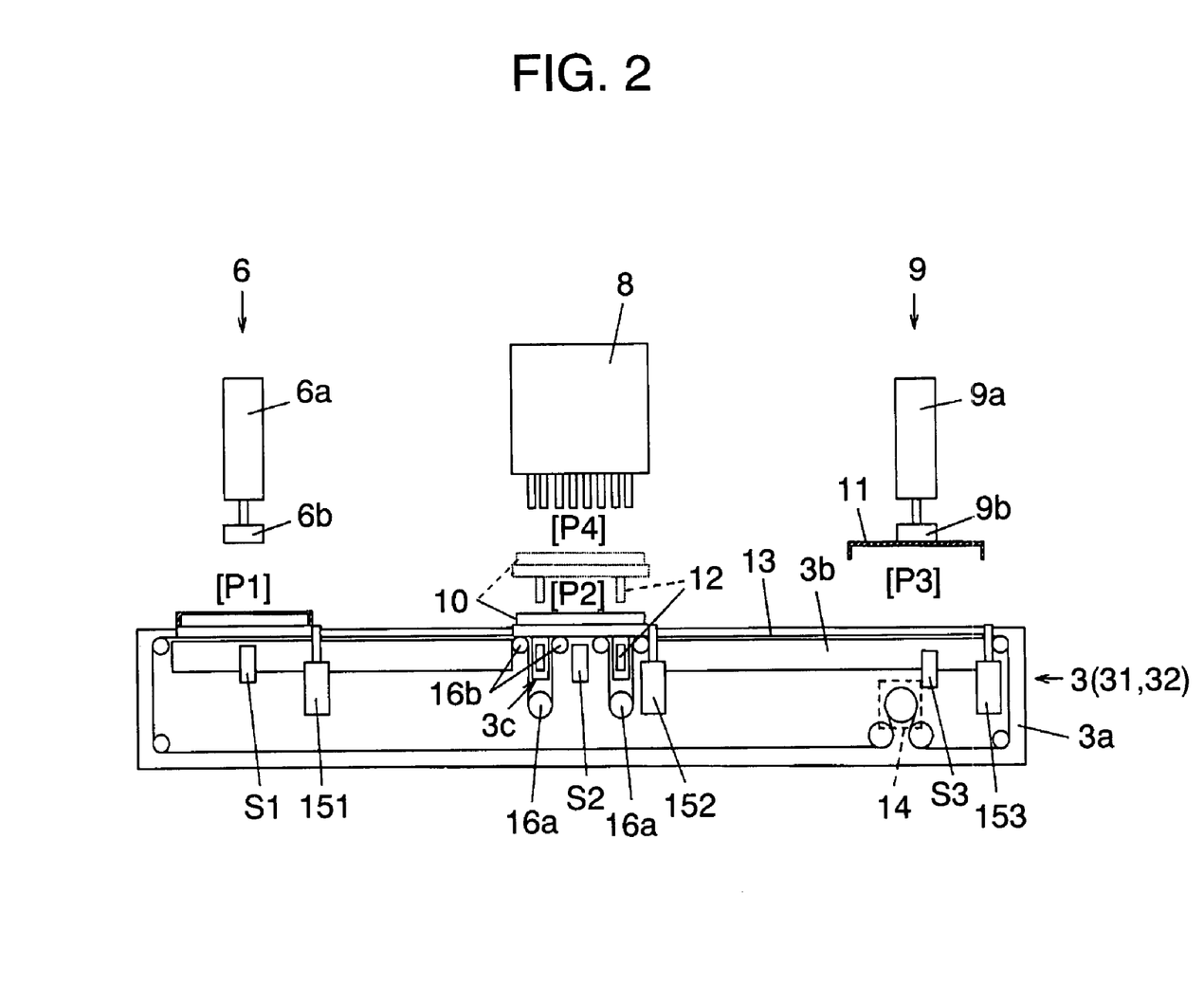
FIG. 2 is a front view of the microplate processing apparatus according to the embodiment.
Figure 3:
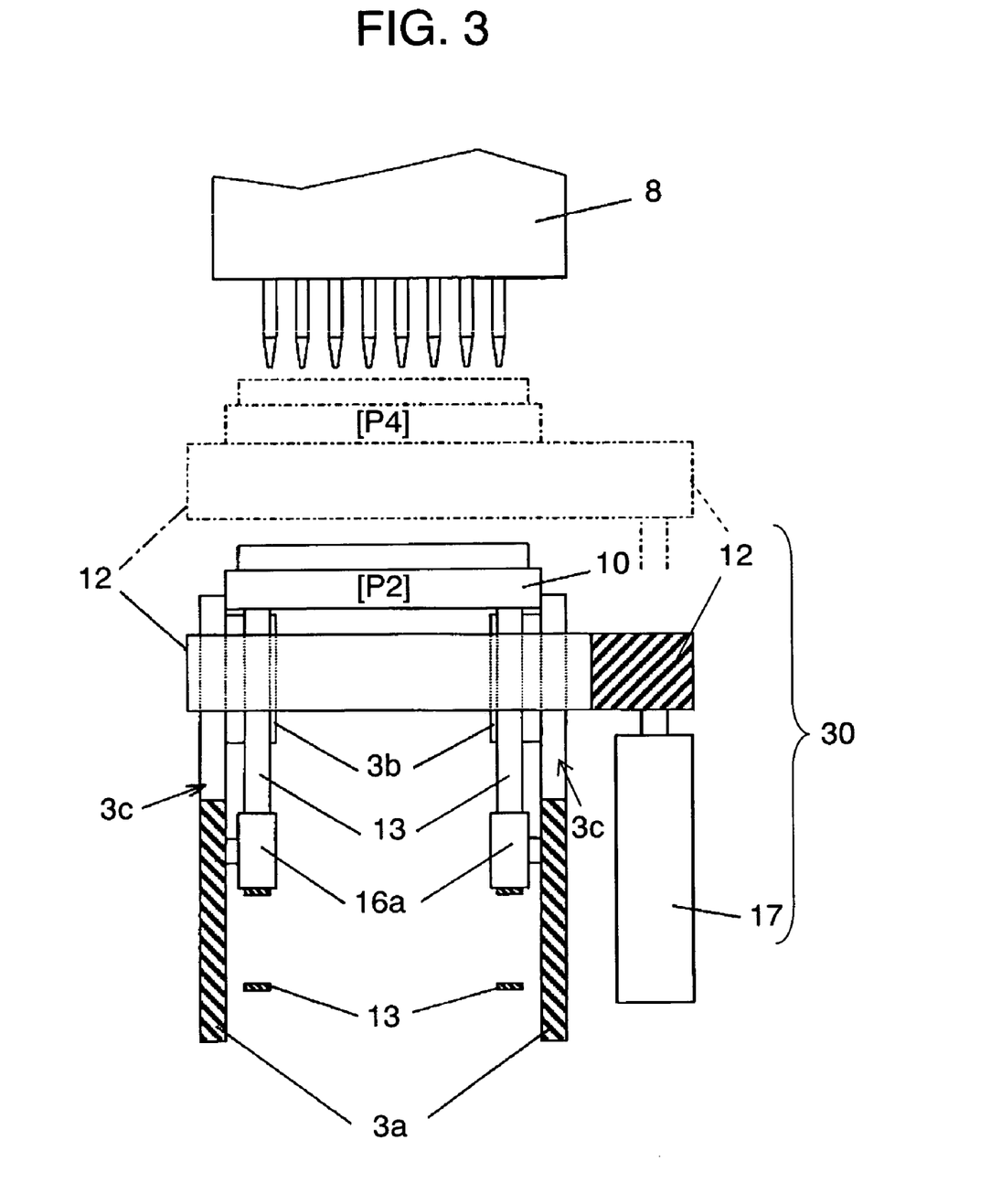
FIG. 3 is a partially sectional view of the microplate conveying mechanism in the microplate processing apparatus according to the embodiment.

FIG. 1 is a perspective view of a microplate processing apparatus according to an embodiment of the present invention; FIG. 2, a front view of the microplate processing apparatus according to the embodiment; FIG. 3, a partially sectional view of the microplate conveying mechanism in the microplate processing apparatus according to the embodiment; and FIG. 4, a block diagram illustrating the makeup of the control system of the microplate processing apparatus according to the embodiment. FIGS. 5A through 5D, FIGS. 6A through 6D, FIGS. 7A through 7D, and FIG. 8 are explanatory diagrams for the operation of the microplate processing apparatus according to the embodiment.

First, a description will be made for the entire structure of microplate processing apparatus 1, referring to FIG. 1. Microplate processing apparatus 1, in biochemical testing and analysis such as in drug screening, has functions for removing a microplate lid to perform a given process for the microplate, and for attaching the lid after the process is completed.

As shown in FIG. 1, in microplate processing apparatus 1, first microplate conveying mechanism 31 and second microplate conveying mechanism 32, both having the identical structure, are horizontally arranged on base 2 in parallel with each other; and dispensing head 8, movable owing to dispensing head drive mechanism 7, is allocated above these microplate conveying mechanisms. Further, first plate feeding container 41 and first plate collecting container 51 are arranged at both ends of first microplate conveying mechanism 31; second plate feeding container 42 and second plate collecting container 52, at both ends of second microplate conveying mechanism 32.

Microplates 10 as test objects are contained in first plate feeding container 41 and second plate feeding container 42. Microplates 10 fed one by one from first plate feeding container 41 and second plate feeding container 42, are conveyed downstream (to the right in FIG. 1) by means of first microplate conveying mechanism 31 and second microplate conveying mechanism 32, both with conveyor belts.

Then, a dispensing operation is performed for microplates 10 by dispensing head 8, on the conveying paths of first microplate conveying mechanism 31 and second microplate conveying mechanism 32. Microplates 10 having undergone the dispensing operation are conveyed downstream by first microplate conveying mechanism 31 and second microplate conveying mechanism 32, and collected to first plate collecting container 51 and second plate collecting container 52.

Microplate 10 as a test object is to be stocked with lid 11 attached, to prevent foreign matter from being immixed, and thus lid 11 is attached and detached when dispensing operation is performed by dispensing head 8. Accordingly, microplate processing apparatus 1 is provided with lid removing mechanism 6 and lid attaching mechanism 9 for removing and attaching lid 11, upstream and downstream of dispensing head 8, respectively. Lid removing mechanism 6 and lid attaching mechanism 9 move up and down first lid holding head 6b and second lid holding head 9b, both capable of sucking and holding lid 11, by means of first lid holding head up/down actuator 6a and second lid holding head up/down actuator 9a, respectively.

Next, a description is made for the structures of first microplate conveying mechanism 31 and second microplate conveying mechanism 32, and for their positional segments on the conveying path, referring to FIG. 2.

As shown in FIG. 2, first microplate conveying mechanism 31 and second microplate conveying mechanism 32 (hereinafter, collectively described as "microplate conveying mechanism 3" as long as discrimination is not required) have two pieces of guide plates 3a, arranged so as to face each other vertically in the conveying direction, as the frame of the conveyor body, and belt 13 driven by conveyor belt drive motor 14 travels on bearing plates 3*b*, horizontally provided in respective guide plates 3*a*.

The top surface of belt 13 born by bearing plate 3*b* for travel is a conveying path which microplate 10 is placed on and conveyed through. The traveling direction of belt 13, namely the conveying direction, and the start/stop timing of conveying are arbitrarily controllable as required. The conveying path of microplate conveying mechanism 3 has the positions thereon with enough sizes for each one microplate 10 to stay in, located upstream, downstream, and centrally: first position [P1], second position [P2], and third position [P3].

First position [P1] is a lid removing position for removing lid 11 from microplate 10 by lid removing mechanism 6, as well as for receiving microplate 10 fed from plate feeding containers 41 and 42 located upstream. Third position [P3] is a lid attaching position for reattaching lid 11 once removed at first position [P1], to microplate 10. Finally, second position [P2], located intermediately between first position [P1] and third position [P3], is an intermediate position for extracting microplate 10 from microplate conveying mechanism 3 to perform a dispensing process for microplate 10 by dispensing head 8, as described later.

First position [P1], second position [P2], and third position [P3] are provided with first stopper 151, second stopper 152, and third stopper 153, respectively, for stopping microplate 10 at each position. The respective positions are provided with sensors for detecting the presence of microplate 10 at each position: first sensor S1, second sensor S2, and third sensor S3. In other words, microplate conveying mechanism 3 is equipped with a plurality of stoppers for stopping microplate 10 by contacting an end of the microplate at first position [P1], second position [P2], and third position [P3] (lid removing position, intermediate position, and lid attaching position, respectively).

Next, a description is made for a microplate stage provided at second position [P2].

As shown in FIG. 2, notched groove 3*c* is formed vertically at the central part of guide plate 3*a*. Belt 13 travels around notched groove 3*c* by means of pulleys 16*a* and 16*b*. As shown in FIG. 3, microplate stage 12 with its horizontal top surface is arranged in notched groove 3*c* in a vertically insertable and removable manner. Microplate stage 12 is movable up and down by means of microplate stage up/down actuator 17 arranged behind guide plate 3*a*. Microplate stage up/down actuator 17 is an up/down mechanism for microplate stage 12.

Microplate stage 12 is positioned so as not to prevent microplate 10 from being conveyed by belt 13 while microplate stage 12 is down in notched groove 3*c*. As a result that microplate stage up/down actuator 17 is driven while microplate 10 is positioned at second position [P2], to elevate microplate stage 12, microplate 10 is raised by microplate stage 12, to allow positioning to processing position [P4], where a dispensing process is performed by dispensing head 8.

In other words, the position where microplate stage 12 is elevated by microplate stage up/down actuator 17 falls at processing position [P4], where a dispensing process is performed. After the dispensing process is completed, as a result that microplate stage 12 is moved down by microplate stage up/down actuator 17, microplate 10 having undergone the dispensing process returns onto the conveying path of microplate conveying mechanism 3, at second position [P2].

In the above-mentioned makeup, microplate conveying mechanism 3 conveys microplate 10 with a conveyor belt in the order corresponding to first position [P1], second position [P2], and third position [P3] (lid removing position, intermediate position, and lid attaching position, respectively) from the upstream on the conveying path. Further, aforementioned microplate stage 12 extracts microplate 10 conveyed by microplate conveying mechanism 3, from microplate conveying mechanism 3, at second position [P2]; positions microplate 10 to processing position [P4], where a dispensing process is to be performed; and becomes a component of microplate positioning mechanism 30 that replaces microplate 10 from relevant processing position [P4] to microplate conveying mechanism 3. In this embodiment, microplate stage 12 that supports microplate 10 from an under side, and up/down mechanism (microplate stage up/down actuator) 17 that moves this microplate stage 12 up and down compose microplate positioning mechanism 30.

Dispensing head 8 is a processing unit that performs a given process for microplate 10 positioned at processing position [P4]. Lid removing mechanism 6 removes lid 11 of microplate 10 conveyed by microplate conveying mechanism 3, at first position [P1], and places the removed lid 11 on the conveying path of microplate conveying mechanism 3. Lid attaching mechanism 9 picks up lid 11 conveyed from first position [P1] to third position [P3] by microplate conveying mechanism 3, from microplate conveying mechanism 3, and attaches the picked up lid 11, to microplate 11 conveyed to third position [P3] by microplate conveying mechanism 3.

Figure 4:
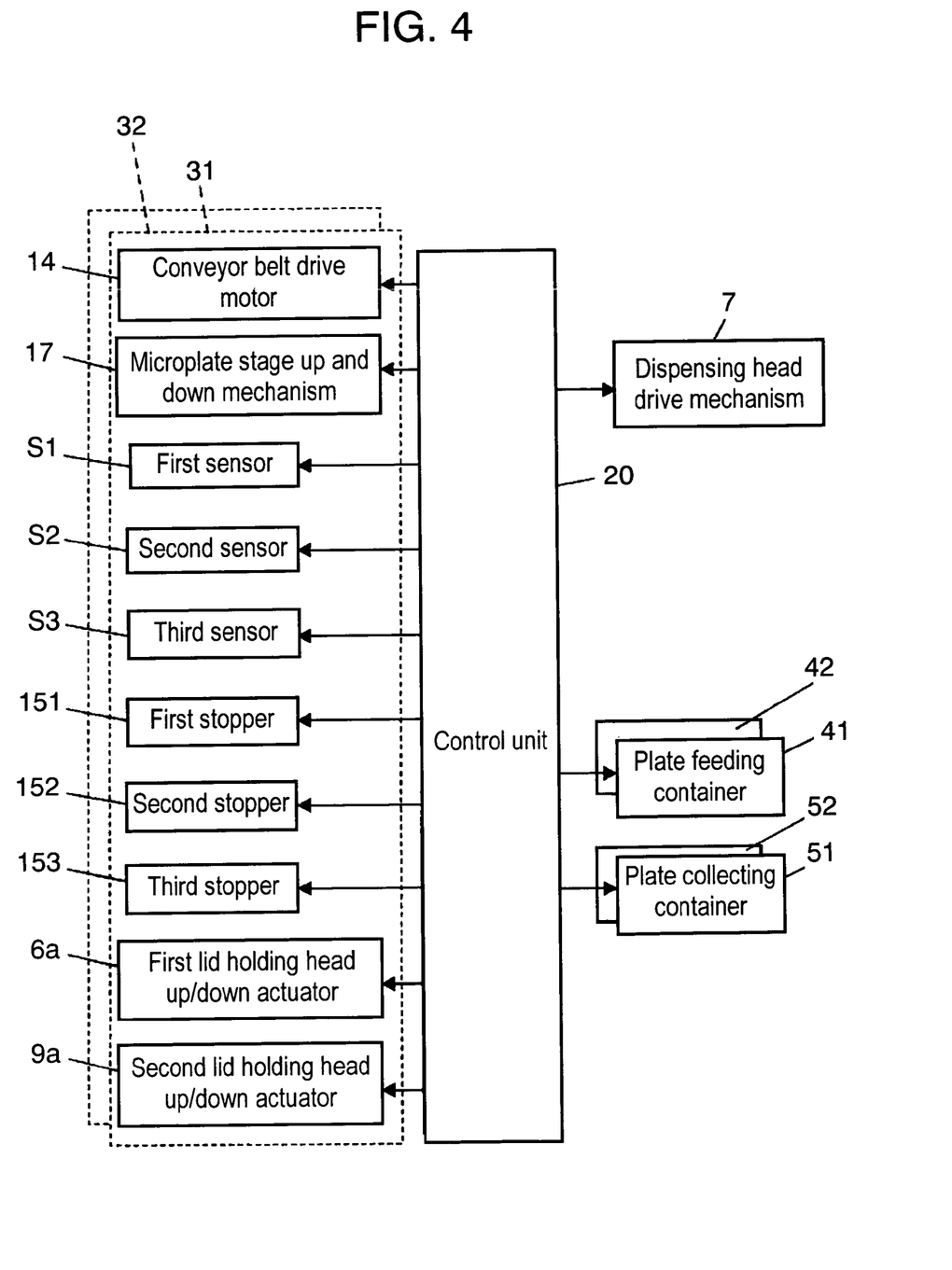
FIG. 4 is a block diagram illustrating the makeup of the control system of the microplate processing apparatus according to the embodiment.

Next, a description will be made for the makeup of the control system, referring to FIG. 4. FIG. 4 specifically shows only the components of first microplate conveying mechanism 31, out of the respective components of first microplate conveying mechanism 31 and second microplate conveying mechanism 32. Control unit 20 controls the operations of conveyor belt drive motor 14, microplate stage up/down actuator 17, first stopper 151, second stopper 152, and third stopper 153, in the plate conveying operation by first microplate conveying mechanism 31 and second microplate conveying mechanism 32. At this moment, the detection results of first sensor S1, second sensor S2, and third sensor S3 are referred to.

Additionally, control unit 20 controls first lid holding head up/down actuator 6*a* and first lid holding head 6*b*, for attaching and detaching operations of lid 11 performed during the plate conveying operation. Control unit 20 further controls the moving operation of dispensing head 8 during the dispensing process for microplate 10, by controlling dispensing head drive mechanism 7; and controls feeding and collecting operations of microplate 10, by controlling first plate feeding container 41 and second plate feeding container 42.

Next, a description will be made for the plate conveying operation by means of control unit 20.

In a plate process by means, of microplate processing apparatus 1, microplate 10 is conveyed to second position [P2] after lid 11 is removed from microplate 10 fed with lid 11 attached, by lid removing mechanism 6. Subsequently, microplate 10 extracted from second position [P2] is positioned to processing position [P4], where a dispensing operation is performed by dispensing head 8, by the aforementioned microplate positioning mechanism 30. Then, microplate 10 is replaced from processing position [P4] onto the conveying path of microplate conveying mechanism 3, after the dispensing process by dispensing head 8 is completed. Further, lid 11 is to be attached to microplate 10 conveyed to third position [P3], by lid attaching mechanism 9.

Here, the correspondence between microplate 10 and lid 11 is not in random order, but lid 11 that was attached when fed is to be always attached to its original microplate 10, in order to prevent foreign matter from being immixed into microplate 10. Accordingly, in microplate processing apparatus 1 according to this embodiment, lid 11 removed at first position [P1] is conveyed to third position [P3] in advance of microplate 10, and is preliminarily held in lid attaching mechanism 9. Then, the lid 11 is to be attached to microplate 10, when microplate 10 having undergone the process is conveyed to third position [P3].

In order to implement these lid attaching and detaching operations by the same microplate conveying mechanism 3, the aforementioned microplate stage 12 is provided at second position [P2], and lid 11 is to be conveyed to third position [P3] in advance while microplate 10 is being elevated and extracted from microplate conveying mechanism 3.

Figure 5A:
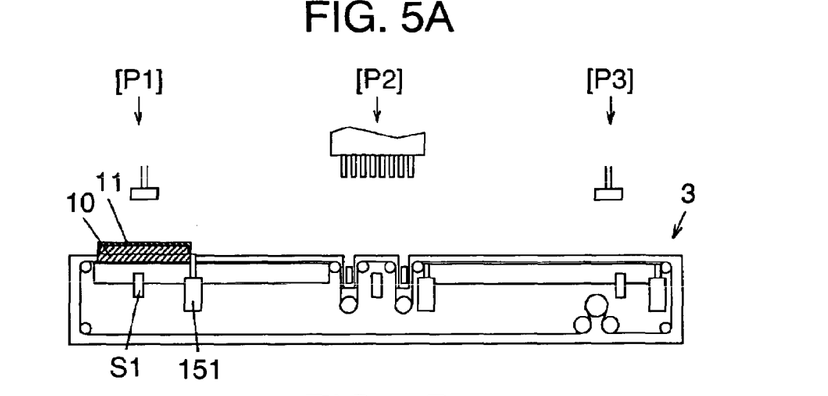
FIG. 5A is an explanatory diagram for the operation of the microplate processing apparatus according to the embodiment.

Microplate processing apparatus 1 is composed as mentioned above. Hereinafter, a description will be made for a method of conveying microplates in microplate processing apparatus 1, referring to FIGS. 5A through 8. When starting the process in microplate processing apparatus 1, microplate 10 fed from first plate feeding container 41 or second plate feeding container 42, is placed on first position [P1] with lid 11 attached, as shown in FIG. 5A, and is stopped at first position [P1] by first stopper 151 preliminarily elevated. In other words, microplate 10 with lid 11 attached is conveyed to first position [P1] (lid removing position), by microplate conveying mechanism 3 (lid removing position conveying step).

Figure 5B:
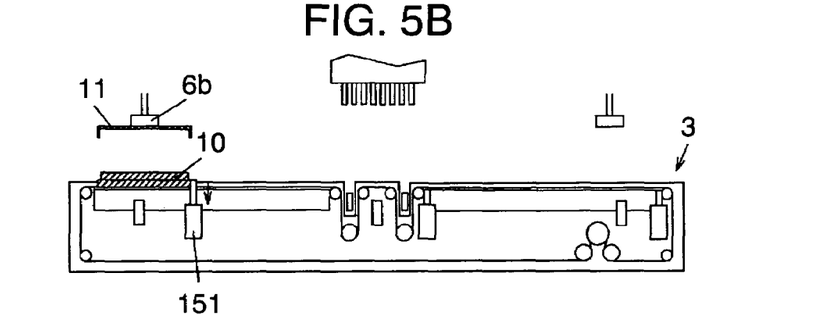
FIG. 5B is an explanatory diagram for the operation of the microplate processing apparatus according to the embodiment.

Here, when a given standby time elapses after first sensor S1 detects microplate 10, first lid holding head 6b moves up and down, to remove lid 11 from microplate 10, as shown in FIG. 5B. That is, lid 11 is removed from microplate 10 at first position [P1] (lid removing position) (lid removing step).

Figure 5C:
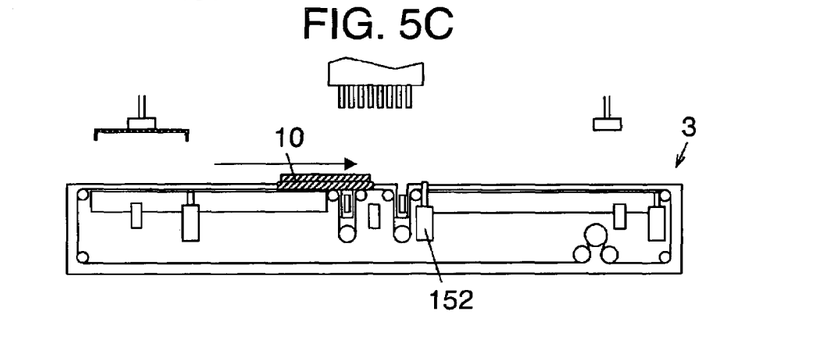
FIG. 5C is an explanatory diagram for the operation of the microplate processing apparatus according to the embodiment.
Figure 5D:
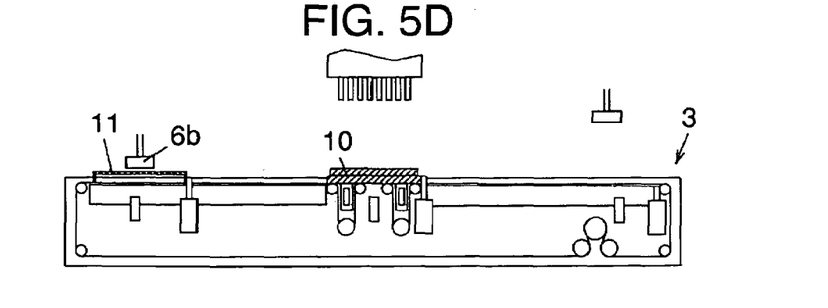
FIG. 5D is an explanatory diagram for the operation of the microplate processing apparatus according to the embodiment.

After then, first stopper 151 is released; microplate 10 with lid 11 removed is conveyed to second position [P2], as shown in FIG. 5C; and microplate 10 is stopped at second position [P2] by means of second stopper 152 preliminarily elevated. In other words, microplate 10 with lid 11 removed is conveyed to second position [P2] (intermediate position), by means of microplate conveying mechanism 3 (intermediate position conveying step).

If second sensor S2 detects microplate 10 at this moment, belt 13 is stopped after its travel speed is reduced to extract microplate 10. Further, with the detection by second sensor S2, first stopper 151 is elevated, and then lid 11 having been held in first lid holding head 6b is placed on the conveying path of microplate conveying mechanism 3, at first position [P1]. In other words, lid 11 having been removed in the lid removing step is placed on the conveying path of microplate conveying mechanism 3 (lid placing step).

Figure 6A:
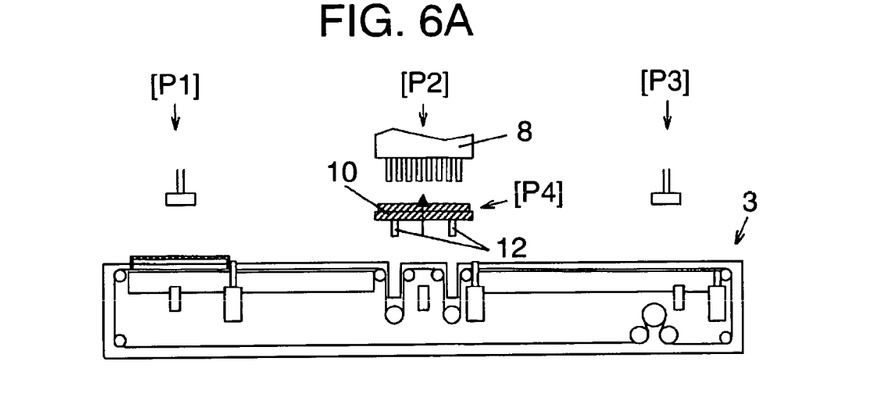
FIG. 6A is an explanatory diagram for the operation of the microplate processing apparatus according to the embodiment.

When a given time elapses after microplate 10 is detected by second sensor S2, first lid holding head 6b is elevated as shown in FIG. 6A, while microplate stage 12 is elevated at second position [P2] to lift microplate 10, and microplate 10 is positioned at processing position [P4], where a dispensing process is performed by dispensing head 8. In other words, microplate 10 conveyed to second position [P2] is extracted from microplate conveying mechanism 3 and positioned at processing position [P4] (positioning step).

Figure 6B:
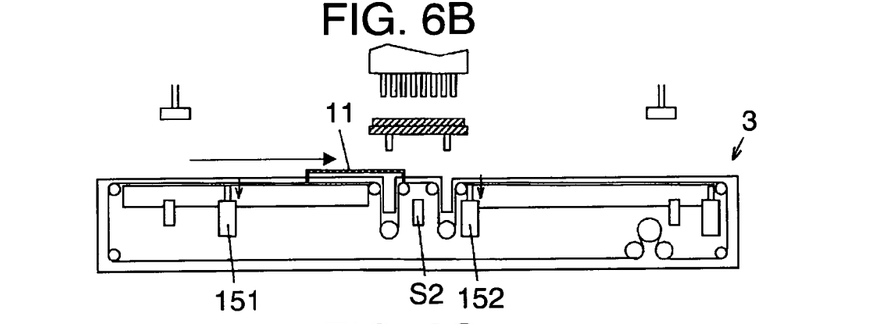
FIG. 6B is an explanatory diagram for the operation of the microplate processing apparatus according to the embodiment.
Figure 6C:
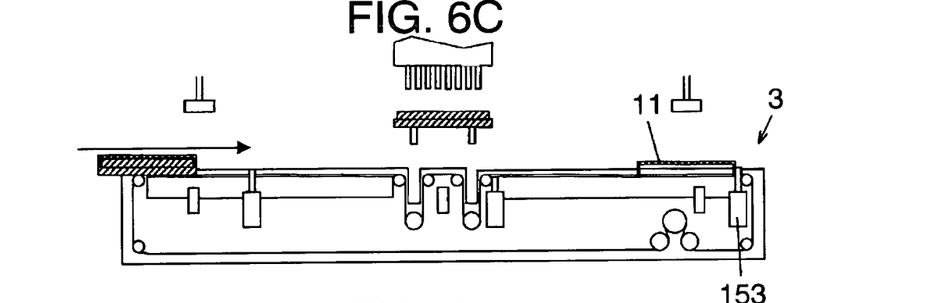
FIG. 6C is an explanatory diagram for the operation of the microplate processing apparatus according to the embodiment.

Subsequently, as shown in FIG. 6B, first stopper 151 and second stopper 152 are released to convey lid 11 further downstream through first position [P1] and second position [P2]. At this moment, when second sensor S2 detects that lid 11 has passed through, first stopper 151 and third stopper 153 are elevated. Then, as shown in FIG. 6C, lid 11 is stopped at third position [P3] by means of third stopper 153 preliminarily elevated. In other words, lid 11 placed on microplate conveying mechanism 3 is conveyed from first position [P1] to third position [P3] by microplate conveying mechanism 3 (lid conveying step).

Figure 6D:
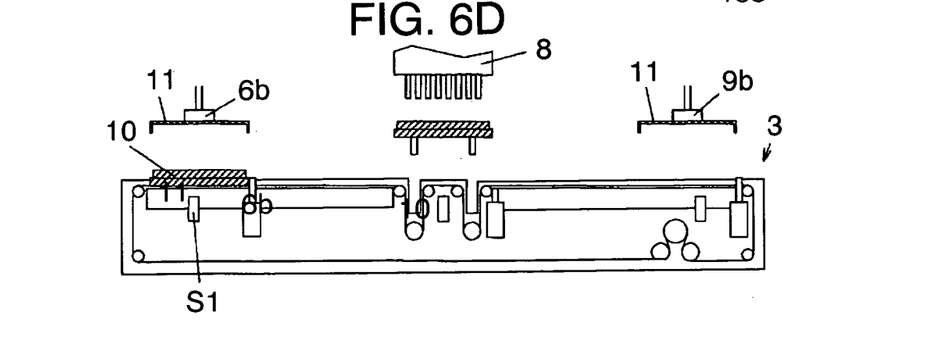
FIG. 6D is an explanatory diagram for the operation of the microplate processing apparatus according to the embodiment.

Along with the above operation, first position [P1] is fed with new microplate 10, which is stopped by first stopper 151 preliminarily elevated. After then, when a given time elapses after microplate 10 is detected by first sensor S1, lid 11 is removed from microplate 10 by first lid holding head 6b, at first position [P1], as shown in FIG. 6D.

Along with this operation, when a given time elapses after lid 11 is detected by third sensor S3, lid 11 on the conveying path is picked up by second lid holding head 9b, at third position [P3]. In other words, lid 11 conveyed to third position [P3] is picked up from microplate conveying mechanism 3 to be held (lid picking up step).

Figure 7A:
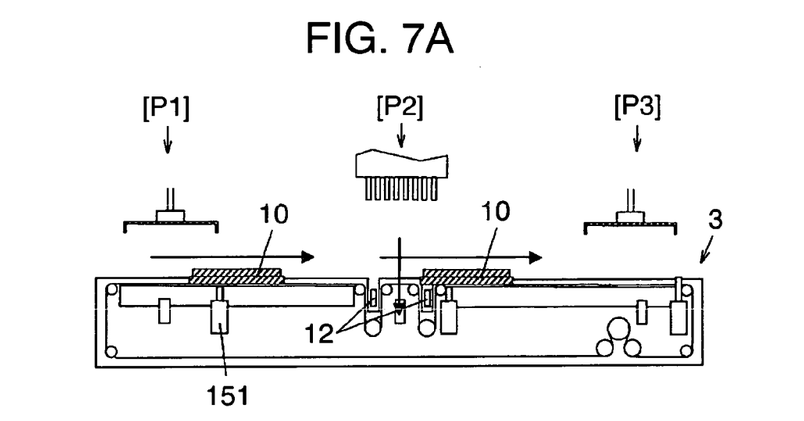
FIG. 7A is an explanatory diagram for the operation of the microplate processing apparatus according to the embodiment.

After then, the completion of the dispensing process by dispensing head 8 is waited. When the dispensing process is completed, first stopper 151 is released while microplate stage 12 is moved down and microplate 10 having undergone the dispensing process is replaced to second position [P2], as shown in FIG. 7A. In other words, microplate 10 having undergone a given process at processing position [P4] is replaced to microplate conveying mechanism 3, at second position [P2] (microplate replacing step).

Figure 7B:
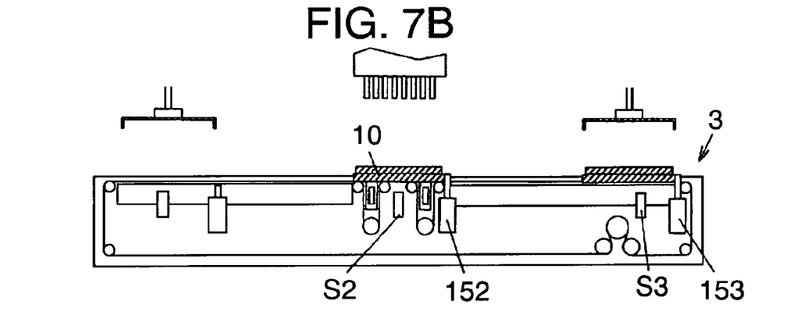
FIG. 7B is an explanatory diagram for the operation of the microplate processing apparatus according to the embodiment.

After then, belt 13 travels to start a conveying operation of microplate 10 by microplate conveying mechanism 3. This operation causes new microplate 10 to be conveyed downstream from first position [P1]; and microplate 10 having undergone dispensing, downstream from second position [P2]. In other words, microplate 10 replaced to microplate conveying mechanism 3 is conveyed from second position [P2] to third position [P3] (lid attaching position) by microplate conveying mechanism 3 (lid attaching position conveying step). Then, these microplates 10 stop at second position [P2] and third position [P3] by second stopper 152 and third stopper 153 preliminarily elevated, respectively, as shown in FIG. 7B.

Figure 7C:
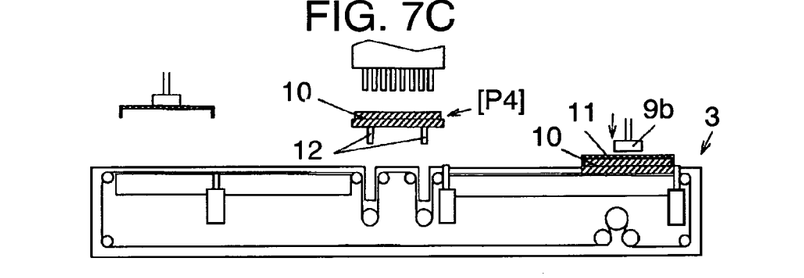
FIG. 7C is an explanatory diagram for the operation of the microplate processing apparatus according to the embodiment.

Next, at second position [P2], when a given time elapses after microplate 10 is detected by second sensor S2, microplate stage 12 is elevated to lift microplate 10, as shown in FIG. 7C. Meanwhile, at third position [P3], when a given time elapses after microplate 10 is detected by third sensor S3, lid 11 having been held by second lid holding head 9b is attached to microplate 10. In other words, lid 11 held in the lid picking up step is attached to microplate 10 conveyed to a lid attaching position (lid attaching step).

Figure 7D:
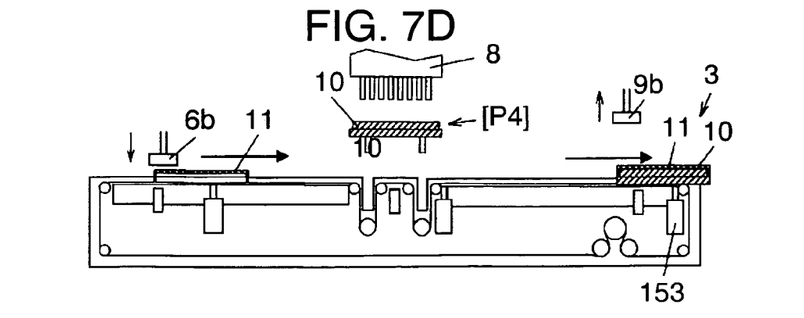
FIG. 7D is an explanatory diagram for the operation of the microplate processing apparatus according to the embodiment.

After then, at first position [P1], lid 11 having been held by first lid holding head 6b is replaced onto the conveying path of microplate conveying mechanism 3 to be conveyed downstream, while at third position [P3], third stopper 153 is released after second lid holding head 9b is elevated to convey microplate 10 with lid 11 attached, downstream, as shown in FIG. 7D. In other words, microplate 10 with lid 11 attached is carried out from third position [P3] by microplate conveying mechanism 3 (carrying out step). At processing position [P4], above second position [P2], a dispensing process by dispensing head 8 is started.

Figure 8:
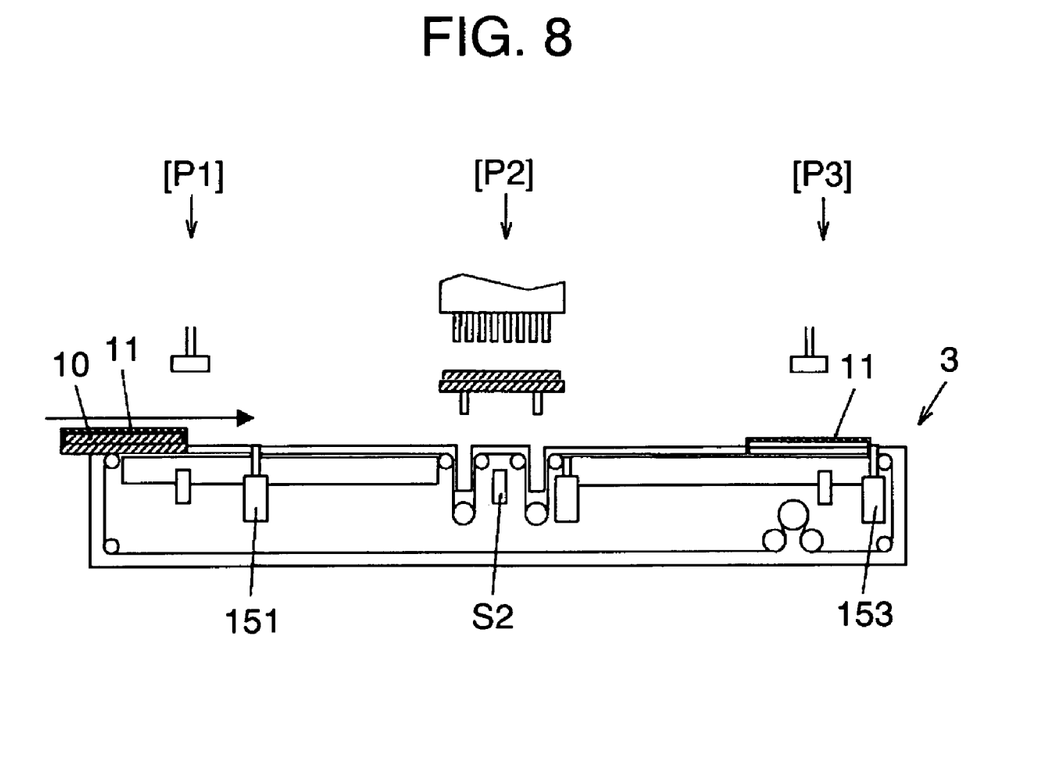
FIG. 8 is an explanatory diagram for the operation of the microplate processing apparatus according to the embodiment.

After then, when second sensor S2 detects that lid 11 has passed through, first stopper 151 and third stopper 153 are elevated. This operation brings the same state as in FIG. 6C, as shown in FIG. 8, causing the same operation to be iteratively executed from then on. Further, the lid conveying step in above-mentioned plate conveying operation 3 is to be executed within the time from when microplate 10 is extracted from microplate conveying mechanism 3 in the positioning step, until when the microplate replacing step is completed. Still, lid 11 removed from microplate 10 in the lid removing step is attached to original microplate 10 with lid 11 having been attached in the lid attaching step.

As mentioned above, as a result that processing position [P4], where a given process is performed, targeted for microplate 10 with lid 11 extracted at first position [P1], is set above microplate conveying mechanism 3, lid 11 can be conveyed from first position [P1] to third position [P3] in advance of microplate 10, while microplate 10 is being extracted from microplate conveying mechanism 3 by microplate positioning mechanism 30.

This makeup allows lid 11 to be attached to original microplate 10 having undergone a process, and to be attached and detached efficiently in a microplate processing apparatus that performs processes while continuously conveying a large number of microplates 10 by a single microplate conveying mechanism.

INDUSTRIAL APPLICABILITY

A microplate processing apparatus according to the present invention is effective in that the lid of a microplate is efficiently attached to and detached from the microplate, for continuous processes targeted for a microplate requiring a lid to be attached.

REFERENCE NUMERALS IN THE DRAWINGS

1 Microplate processing apparatus
3 Microplate conveying mechanism
6 Lid removing mechanism
8 Processing unit (Dispensing head)
9 Lid attaching mechanism
10 Microplate
11 Lid
12 Microplate stage
17 Microplate stage up and down mechanism
20 Control unit
30 Microplate positioning mechanism 151, 152, 153 Stopper
P1 First position (Lid removing position)
P2 Second position (Intermediate position)
P3 Third position (Lid attaching position)
P4 Processing position

The invention claimed is:

1. A microplate processing apparatus for a microplate with a lid, the apparatus comprising:
a conveying unit, including a conveyor belt adapted to convey the microplate and lid to a plurality of positions in an order corresponding to a lid removing position, an intermediate position, and a lid attaching position;
a sensor for detecting the presence of the microplate at the intermediate position;
a microplate positioning unit adapted to extract the microplate from the conveyor belt at the intermediate position to a processing position, and replace the microplate from the processing position to the conveyor belt;
a processing unit adapted to perform a given process on the contents of the microplate when the microplate is at the processing position;
a lid removing unit adapted to remove the lid of the microplate at the lid removing position, hold the lid, and place the lid on the conveyor belt in response to the sensor detecting the presence of the microplate at the intermediate position while the lid removing unit is holding the lid;
a lid attaching unit adapted to pick up the lid from the conveyor belt when the lid is at the lid attaching position, hold the lid, and attach the lid to the microplate when the microplate is at the lid attaching position.

2. The microplate processing apparatus of claim 1, wherein the microplate positioning unit includes a microplate stage that supports the microplate from an under side; and an up/down mechanism that moves the microplate stage up and down.

3. The microplate processing apparatus of claim 1, wherein the conveying unit includes a plurality of stoppers that stop the microplate or the lid at the lid removing position, the intermediate position, and the lid attaching position, by contacting an end of the microplate or lid.

4. A method of conveying a microplate in a microplate processing apparatus including a conveyor belt, that conveys the microplate and lid in an order corresponding to a lid removing position, an intermediate position, and a lid attaching position, the method comprising:
a lid removing position conveying step for conveying the microplate with a lid thereof attached to the lid removing position, by the conveyor belt;
a lid removing step for removing the lid of the microplate at the lid removing position;
an intermediate position conveying step for conveying the microplate, with the lid removed, to the intermediate position, by the conveyor belt;
a positioning step for extracting the microplate from the intermediate position to a processing position;
a processing step for performing a given process on the microplate at the processing position;
a lid placing step for placing the lid removed in the lid removing step onto the conveyor belt;
a lid conveying step for conveying the lid placed onto the conveyor belt, from the lid removing position to the lid attaching position, by the conveyor belt, at a time when the microplate is extracted from the conveyor belt;
a lid picking up step for picking up the lid conveyed to the lid attaching position, from the conveyor belt, and for holding the lid;
a microplate replacing step for replacing the microplate after the processing step, to the intermediate position;
a lid attaching position conveying step, after the microplate replacing step, for conveying the microplate from the intermediate position to the lid attaching position;
a lid attaching step for attaching the lid, held in the lid picking up step, to the microplate conveyed to the lid attaching position; and
a carrying out step for carrying out the microplate with the lid attached, from the lid attaching position by the conveyor belt.

5. The method of conveying the microplate of claim 4, wherein the lid removed from the microplate in the lid removing step is attached to the original microplate with the relevant lid having been attached in the lid attaching step.

6. The microplate processing apparatus of claim 1, wherein the width of the conveyor belt is approximately equal to a width of the microplate.

* * * * *